(12) United States Patent
Dror

(10) Patent No.: US 9,936,271 B2
(45) Date of Patent: Apr. 3, 2018

(54) SYSTEM AND METHOD FOR PET BEHAVIORAL IDENTIFICATION

(71) Applicant: Oggway Ltd., Tel Aviv (IL)

(72) Inventor: Yonatan Dror, Tel Aviv (IL)

(73) Assignee: Oggway Ltd., Tel Aviv (IL)

( * ) Notice: Subject to any disclaimer, the term of this patent is extended or adjusted under 35 U.S.C. 154(b) by 0 days.

(21) Appl. No.: 15/310,200

(22) PCT Filed: May 11, 2015

(86) PCT No.: PCT/IB2015/053446
§ 371 (c)(1),
(2) Date: Nov. 10, 2016

(87) PCT Pub. No.: WO2015/173712
PCT Pub. Date: Nov. 19, 2015

(65) Prior Publication Data
US 2017/0272843 A1    Sep. 21, 2017

Related U.S. Application Data

(60) Provisional application No. 61/993,640, filed on May 15, 2014.

(51) Int. Cl.
*A01K 29/00*    (2006.01)
*H04Q 9/00*    (2006.01)
(Continued)

(52) U.S. Cl.
CPC .......... *H04Q 9/00* (2013.01); *A01K 29/005* (2013.01); *A61B 5/0002* (2013.01);
(Continued)

(58) Field of Classification Search
CPC . H04A 9/00; G06F 19/345; G06F 9/44; G06F 19/34; A01K 29/005
(Continued)

(56) References Cited

U.S. PATENT DOCUMENTS

2002/0010390 A1*  1/2002  Guice ................. A01K 11/008
600/300
2010/0302004 A1   12/2010  Winstead et al.
(Continued)

FOREIGN PATENT DOCUMENTS

CA          2591902 A1    12/2008

*Primary Examiner* — Albert K Wong
(74) *Attorney, Agent, or Firm* — Gabal Gotwals

(57) ABSTRACT

A system and method for behavioral analysis of a household pet. The system includes a sensor unit having at least one 3D accelerator sensor attached to the pet, a control unit connected with the 3D accelerator sensor and configured to collect acceleration data indicative of selected movements from the sensor. The control unit being configured to perform an initial analysis of the collected sensor data. The system further includes an analysis unit communicating with the control unit, the analysis unit configured to upload the collected sensor data and to receive additional data pertaining at least to the household environment and to the pet's historical condition and to define the pet's condition accordingly by neutralizing the additional data effects, wherein the data collection rate from the sensor is selected in accordance with at least the initial analysis results.

17 Claims, 6 Drawing Sheets

(51) Int. Cl.
*A61B 5/11* (2006.01)
*A61B 5/00* (2006.01)
*G06F 19/00* (2018.01)
*G06N 99/00* (2010.01)

(52) U.S. Cl.
CPC .......... *A61B 5/1118* (2013.01); *G06F 19/345* (2013.01); *G06N 99/005* (2013.01); *A61B 2503/40* (2013.01); *A61B 2560/0242* (2013.01); *H04Q 2209/40* (2013.01); *H04Q 2209/84* (2013.01)

(58) Field of Classification Search
USPC ............... 340/539.01, 539.12; 706/52; 705/2
See application file for complete search history.

(56) References Cited

U.S. PATENT DOCUMENTS

| | | | |
|---|---|---|---|
| 2013/0158686 A1* | 6/2013 | Zhang | G01C 22/006 700/91 |
| 2013/0186962 A1* | 7/2013 | Kennett | G06K 1/128 235/494 |
| 2013/0217979 A1* | 8/2013 | Blackadar | A61B 5/0024 600/301 |
| 2014/0123912 A1 | 5/2014 | Menkes et al. | |
| 2016/0192620 A1* | 7/2016 | Hu | A01K 5/0114 119/51.02 |
| 2017/0097169 A1* | 4/2017 | Azevedo | F24F 11/0034 |
| 2017/0196202 A1* | 7/2017 | Ragonetti | A01K 29/005 |

\* cited by examiner

SYSTEM AND METHOD FOR PET BEHAVIORAL IDENTIFICATION

CROSS-REFERENCE TO RELATED APPLICATIONS

This United States application is the National Phase of PCT Application No. PCT/IB2015/053446 filed 11 May 2015, which claims priority to U.S. Provisional Patent Application No. 61/993,640 filed 15 May 2014, each of which is incorporated herein by reference.

TECHNOLOGICAL FIELD

The invention is in the field of behavioral data identification and is particularly related to identification of behavioral states of pets, dogs for example, based on collected data.

BACKGROUND

There is a need in the art for a technique and corresponding system, capable of monitoring activity of animal pet, analyzing its activity and providing useful and meaningful behavioral and medical data.

There is a connection between pet movement patterns and its health condition.

A household pet by nature, is not an autonomous being, its movement patterns and the trends in the patterns are heavily affected by external influences, mainly by its owners living conditions and daily occurrences. Movement patterns received from a single sensor on a pet are comprised of inherent and externally affected trends and patterns, thus the output is contaminated and causes false positives and negatives. For example:

Assumption: A sick dog with condition X lowers its movement by 20%

False negative: dog owner is very active, thus—dog moves a lot, thus—no change in dog pattern is detected.

False positive: dog owner is sick, thus—his activity lowers by 20%, thus—the dog's activity lowers accordingly, thus—change in dog pattern detected.

Existing pet condition sensing systems fail to neutralize various external effects which influence the pet's sensed measurements and thus are prone to false positive conclusions.

SUMMARY

According to a first aspect of the present invention there is provided a system for behavioral analysis of a household pet, comprising: a primary sensor unit attached to said pet, said sensor unit comprising: at least one 3D accelerator sensor attached to said pet; and a control unit connected with said 3D accelerator sensor and configured to collect acceleration data indicative of selected movements from said sensor, said control unit configured to perform an initial analysis of said collected sensor data; at least one secondary sensor unit configured to sense household environment data pertaining to said pet; and an analysis unit communicating with said control unit and with said at least one secondary sensor unit, said analysis unit configured to upload said collected sensor data and to receive additional data pertaining at least to said household environment and to said pet's historical condition and to define said pet's condition accordingly by neutralizing said additional data effects, wherein the data collection rate from the sensor is selected in accordance with at least said initial analysis results.

The system may further comprise a first electronic communication device (ECD) configured to communicate with said analysis unit, said first ECD configured to receive and store historical condition data for a plurality of pets and to provide said data to said analysis unit.

The system may further comprise a second electronic communication device (ECD) carried by a caretaker selected from said household, said ECD configured to communicate to said analysis unit at least part of said additional data.

The system may further comprise a third electronic communication device (ECD) configured to run a user application for receiving and displaying said analysis results.

The second and third ECDs may comprise a single ECD.

The second ECD may be configured to provide data selected from the group consisting of: global positioning of said caretaker and motion pattern of said caretaker.

The uploading time of said sensor data may be determined according to a learning curve of the proximity times of at least one of the analysis unit and the second ECD to said sensor unit.

The analysis unit may comprise an attribute extraction module configured to extract physical attributes of the pet's behavior.

The physical attributes may comprise head orientation and movement related attributes.

The movement related attributes may comprise at least one of: velocity, energy and power.

The physical attributes may comprise at least one of frequency related attributes and temporal attributes.

According to a second aspect of the present invention there is provided a method of behavioral analysis of a household pet comprising: providing a primary sensor unit attached to said pet; collecting from said primary sensor unit acceleration data indicative of selected movements of said pet; performing an initial analysis of said collected movement data; providing at least one secondary sensor unit; receiving from said at least one secondary sensor unit additional data pertaining at least to said household environment; receiving data pertaining to said pet's historical condition; and defining said pet's condition accordingly by neutralizing said additional data effects, wherein the data collection rate from the sensor is selected in accordance with at least said initial analysis results.

The initial analysis may comprise determining a moving average of the first derivative of the collected acceleration data and determining if the moving average is greater than a predetermined threshold.

Determining the moving average may comprise utilizing varying weights.

The acceleration data may include high frequency varying data and low frequency varying data.

The high frequency varying data may be indicative of the pet's movement, and the low frequency varying data is indicative of orientation of the sensor unit.

Defining said pet's condition may comprise utilizing machine learning.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

The core technology of the present invention utilizes pet's state identification based on movement data (accelerometer data) collected by one or more suitable sensors mounted on the pet and by additional data pertaining to the pet's household environment and optionally additional external sources. The collected data is analyzed by supervised learning to identify the pet's state based on a database. The database may be collected by labeling pet's states and attaching appropriate labels of raw or processed movement data.

Figure 1:
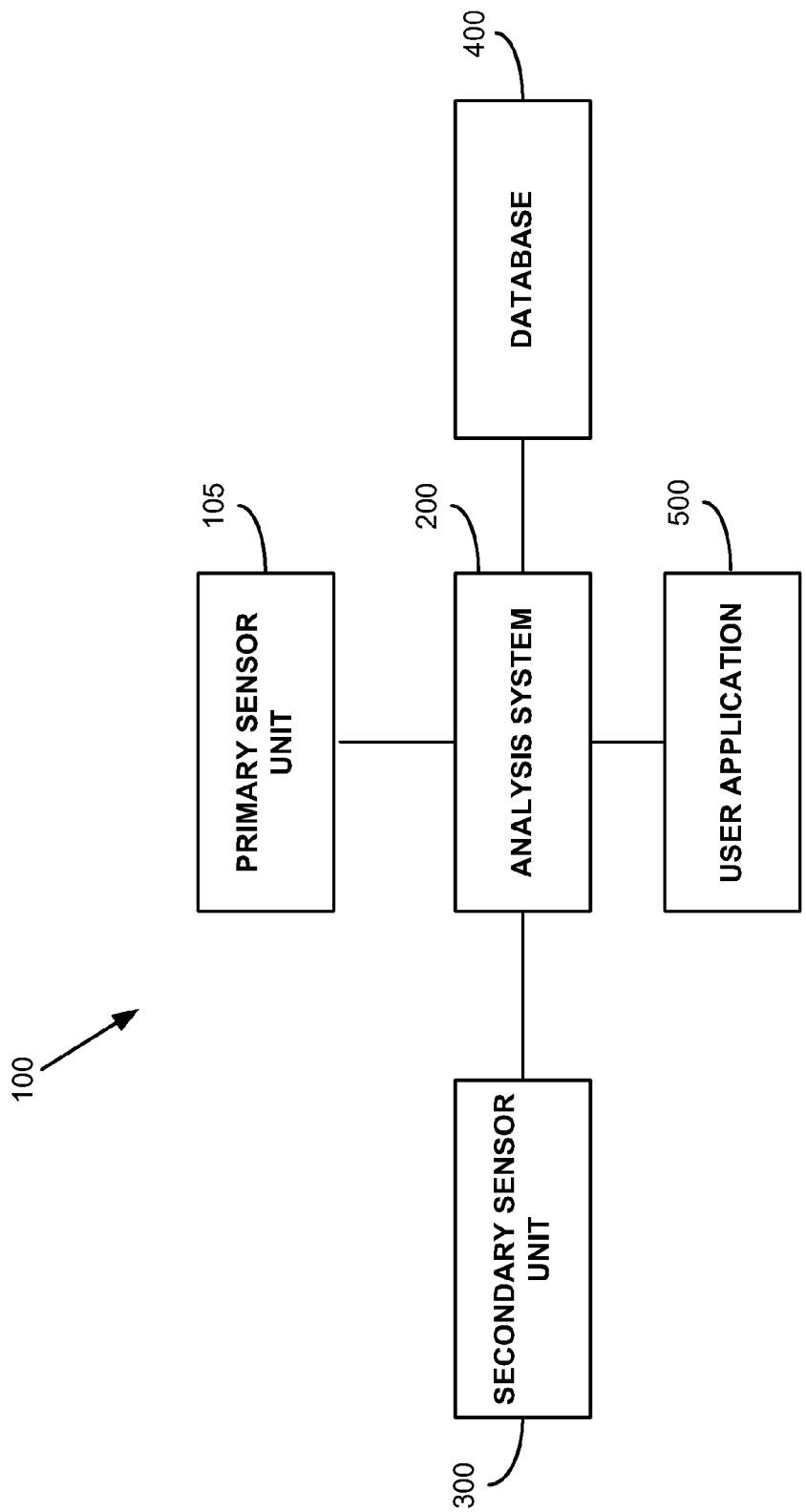
FIG. 1 illustrates schematically an exemplary system according to the present invention.

Reference is made to FIG. 1 schematically illustrating an exemplary system 100 according to the present invention, comprising a primary sensor unit 105 configured to be attached to the pet (e.g. at the collar) and an analysis system 200, as will be explained in detail in conjunction with FIGS. 2A-2B. The system 100 further comprises a at least one secondary sensor unit 300 (e.g. a caretaker's smart phone comprising a positioning sensor) and at least one database 400 (e.g. a database of pets' historical movement data), as will be explained in detail below.

Figure 2A:
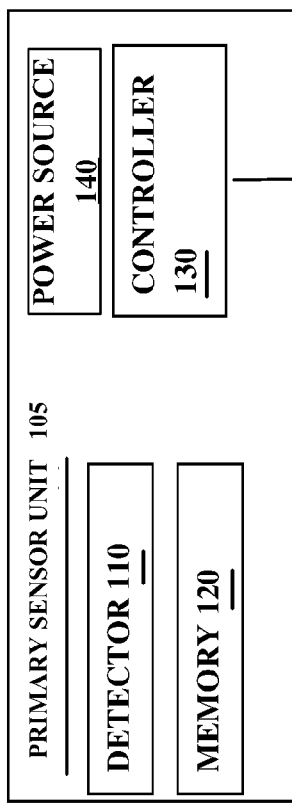
FIGS. 2A-2B illustrate schematically a sensor unit and an analysis system according to the present invention.
Figure 2B:
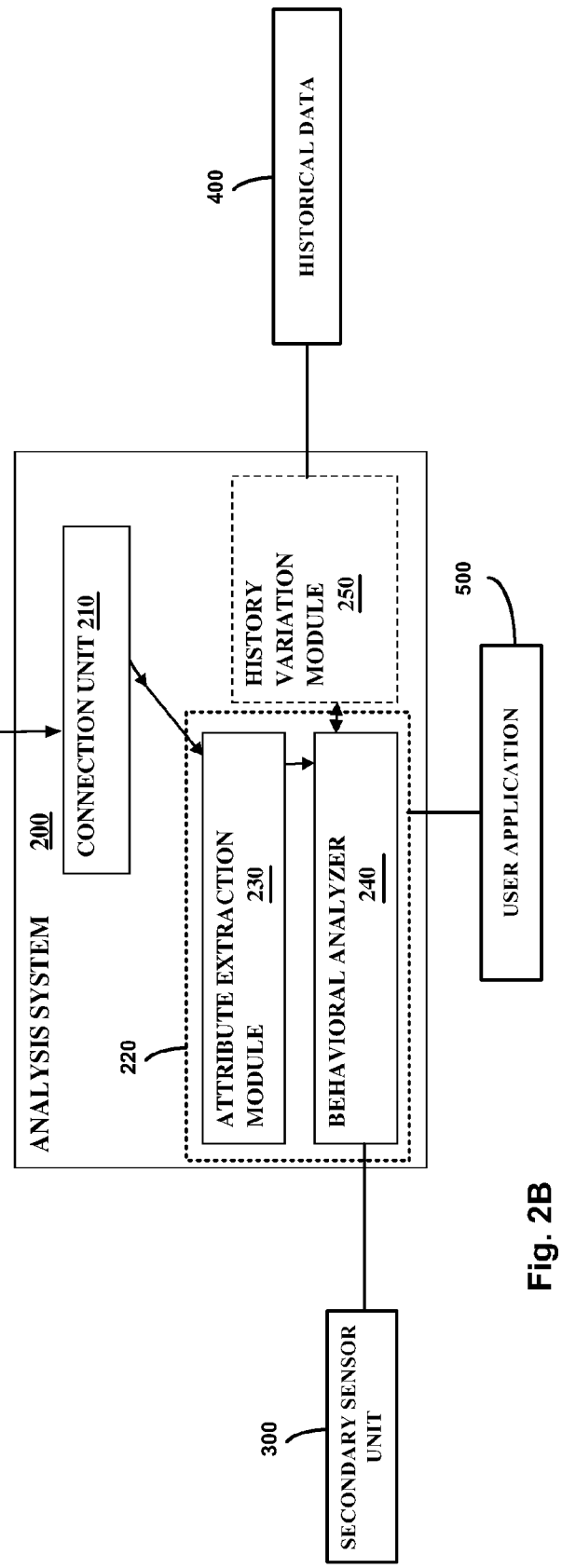

Reference is made to FIGS. 2A-2B schematically illustrating a primary sensor unit 105 (FIG. 2A) and an analysis system 200 (FIG. 2B) according to embodiments of the present invention. The primary sensor unit 105 is generally a light simple unit preferably configured to be mounted on a pet's collar so as not to disturb the pet's movement. The primary sensor unit 105 includes one or more 3D accelerometers 110, memory 120, controller 130, optional power source 140, appropriate connectivity utility possibly an ON/OFF switch (not specifically shown). The primary sensor unit 105 may generally be packed in a sealed package, for example using a sealed plastic or polymeric package, and suitable for attaching to a pet's collar.

The analysis system 200 may be a computerized system being a single unit and/or an aggregated system based on a remotely located server system having a network connection to a local input/output module. The analysis system 200 is configured to receive movement data from the primary sensor unit 105, by wired and/or wireless communication and to analyze the movement data for identification of dog's behavioral states. The analysis system 200 generally includes an input/output connection unit 210, a processing unit 220 which includes an attribute extraction module 230 and a behavioral analyzer 240, the processing unit may also include a history variation module 250.

According to certain embodiments of the invention, the primary sensor unit utilizes a three-dimensional accelerometer sensor/detector 110 generating data about acceleration of the pet along x, y, and z directions in a coordinate system related to the sensor unit. The controller 130 is configured to read the acceleration data from the detector at an appropriate frequency to thereby provide reliable acceleration data. To this end, the controller may perform an initial analysis of the acceleration data, to detect one of a of a number of pre-defined basic conditions such as sleep and activity, based on the read acceleration data and to thereby adjust the readout frequency. For example, the controller may be configured to collect acceleration data at a readout rate of 50 Hz while the dogs is active, and to reduce the readout rate to 10 Hz if it identifies from the dog's movement that it is sleeping.

To this end, the sleep detector may be operated to determine an appropriate data collection rate based on variations in moving average of the change in acceleration. More specifically, if the dog is sleeping, the acceleration data includes mostly the gravity component, which is constant, and thus its derivative is zero. The controller determines a moving average of the first derivative of the collected acceleration data and operates to determine if the moving average is greater than a predetermined threshold or not. If the moving average is determined to be smaller than the predetermined threshold, the dog is assumed to sleep and the collection rate may be reduced. According to some embodiment, the sleep detector may be configured to utilize varying weights for determination of the moving average to thereby provide higher accuracy. More specifically, the sleep detector module may determine values of the moving average of the acceleration derivative in a dual rate, such that if at any point in time the acceleration derivative is greater or smaller than the corresponding average, its weight is determined accordingly. Such dual rate averaging may provide the value of the moving average to converge faster and thus indicate rest states of the dog while avoiding noise related false-positive date.

The controller may also store the collected data at the memory unit 120 and operate to transmit the stored data to the analysis system 200 in response to an appropriate command (e.g. wired connection or proxy based command if wireless connection is used). It should be noted that the controller 130 may compress the collected data to thereby save storage space as well as to reduce communication needs and accelerate data transmission. The controller may for example utilize appropriately optimized ADPCM compression method as known in the art.

The data collected by the primary sensor unit 105 is transmitted to the analysis system 200 either by connecting the primary sensor unit to the analysis system by a cable, or by connection to a computer system, in case the analysis is performed in a remote server. Alternatively, the data may be transferred by wireless connection whenever the primary sensor unit is detected to be in close proximity to the analysis system, or a computer system having appropriate program for communication with the server. According to embodiments of the invention the controller may "learn" times when a caretaker's smart phone storing an appropriate user application is in close proximity and attempt uploading the sensor data to the smart phone which may transmit it to the analysis system.

The same user application 500 may also serve for informing the user (e.g. care taker of the pet) of the pet's condition as determined by the analysis unit. The application may also provide suggestions such as "consult a vet", "give pet more water" etc.

The collected data is in the form of plurality of instant acceleration data providing information about acceleration of the primary sensor unit in three-dimensions. Such acceleration data generally includes high frequency varying data which is generally indicative of the pet's movement, and low frequency varying data which is generally indicative of orientation of the sensor unit thereby providing data about orientation of the head of the pet.

After transmission of the collected data to the analysis system 200 the attribute extraction module 230 utilizes the input data to extract physical attributes of the pet's behavior. Such physical attributes may include head orientation, which may generally be extracted based on gravity-related acceleration data, and movement related attributes such as velocity, energy and power which may be determined based on high-frequency variations of the acceleration data.

In this connection, the collected acceleration data may generally be in the form of 3-dimensional vector (x,y,z) in a coordinate system relating to the sensor unit. For simplicity, the x axis is considered here to face forwards with the pet's head, z axis is down from the pet's head and the y axis relates to side movements. Thus, if the pet is holding its head facing forwards, the gravity related signal can be identified as a non-zero offset in the z coefficient. If the attribute extraction module determines that a low-frequency offset exists in the x coefficient, the dog is assumed to face down, and if such offset is determined in the y coefficient the dog is assumed to lie on its side. Intermediate orientation states can be identified by determination of a polar orientation of the low-frequency offset.

Additional attributes that may be determined by the attribute extraction module 230 generally include the following: moving average acceleration, velocity, power, energy and characteristic frequencies of the dog's acceleration data. More specifically, the moving average acceleration relates to acceleration of the dog to different directions, the moving average acceleration data may be filtered to remove gravity related data. Velocity is determined by short time integration of the acceleration data to thereby provide information indicative of the dog's position, i.e. if the dog is standing still, walking, trotting or running. The power is estimated based on a scalar product of the average acceleration and the velocity to provide data about the power generated by the pet. The energy used by the pet is determined by a short term integration of the power. It should be noted that additional attributes may be determined including frequency related attributes as well as temporal attributes relating to the period of time certain data behavior appears.

The behavioral analyzer 240 also communicates with at least one secondary sensing unit 300 for receiving data pertaining for example to the pet's household environment and other external sensed parameters. Variations in certain sensed household environment parameters may affect the pet's behavior, in which case their influence on the pet's attributes may have to be taken into consideration in determining the pet's condition. For example, the behavioral analyzer 240 may communicate with the pet caretaker's smart phone having GPS functionality and detect absence of the caretaker for a certain period from the home base, which may affect the pet's behavior. In another example, the care taker's smart phone with acceleration sensing functionality and the pet's sensed acceleration data may indicate a joint voyage, which may also affect the pet's behavior or pet owner may be sick and un able to take the pet out for walks, or the entire household's sensed presence or mobility data may indicate changed behavior patterns (for example: due to marriage etc.)

The behavioral analyzer 240 receives attribute data from the attribute extraction module 230, and utilizes appropriate machine learning to determine behavior states of the pet based on these attributes. In this connection the behavioral analyzer 240 may utilize pre-stored data (400, FIG. 1) about the specific pet, e.g. breed, age and weight, as well as pre-stored or external database generated by appropriate learning of this or other pets to determine the behavior states.

In some embodiments short-term pre-stored data may indicate a previously detected condition that may indirectly cause the presently detected behavior. For example, a previously detected leg injury may affect the present movement speed of the pet. Such indirect influence may also have to be In some embodiments the analysis system 200 also includes a history variation module 250, which is configured and operable to determine variation of long term behavior of the dog as compared to previous behavior. Such long time variation data may provide indication of health related issues, aging, obesity etc. For example, if a dog is identified as shaking his head a significant number of time in a day, higher than what he is used to (e.g. 20-30 as compared to normal level of 3-4) the system may suspect ear infection and provide appropriate alert to the owner. Reduced level of energy along a few days may indicate other illnesses which may require treatment etc.

More specifically, reference is made to FIGS. 3-6 illustrating dog's behavioral states with respect to determined attributes.

Figure 3:
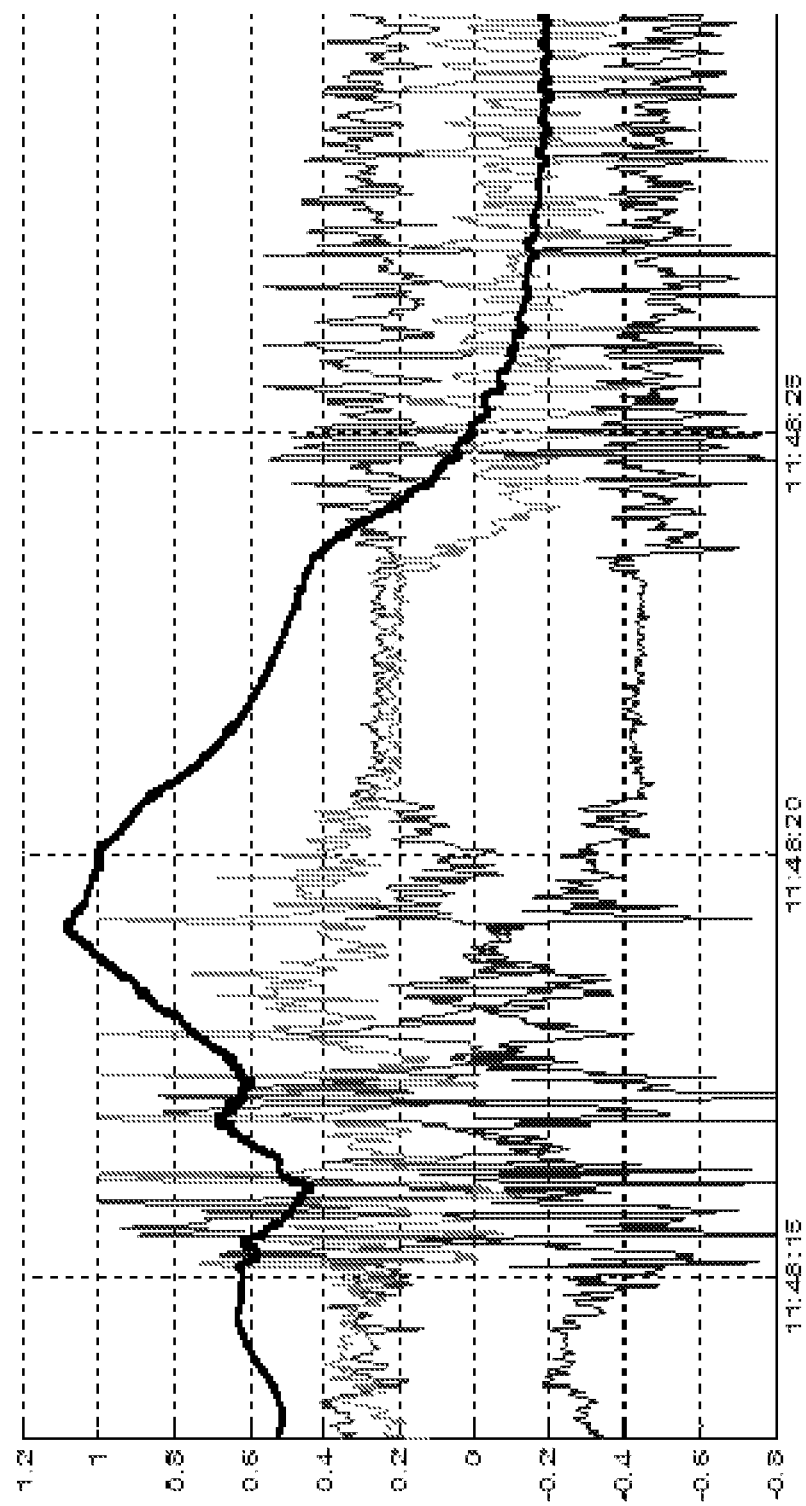
FIGS. 3-6 show dog's behavior attributes as determined by collected movement data according to the present invention.

FIG. 3 illustrates determination of the orientation of the dog's head based on low frequency varying acceleration data. This figure shows acceleration data in x, y and z axes and the head direction attribute as determined based on this data. As can be seen, the dog starts while accelerating to different direction and thus may be excited, additionally, the z component shows low frequency bias to negative acceleration which results from the gravity. After a few seconds, the dog looks up to his food and the head direction changes as a result of higher gravity component in the x data component. The dog than relaxes and waits for his food, and when the dog starts eating, all acceleration along y direction vanishes as he stops wiggling.

Figure 4:
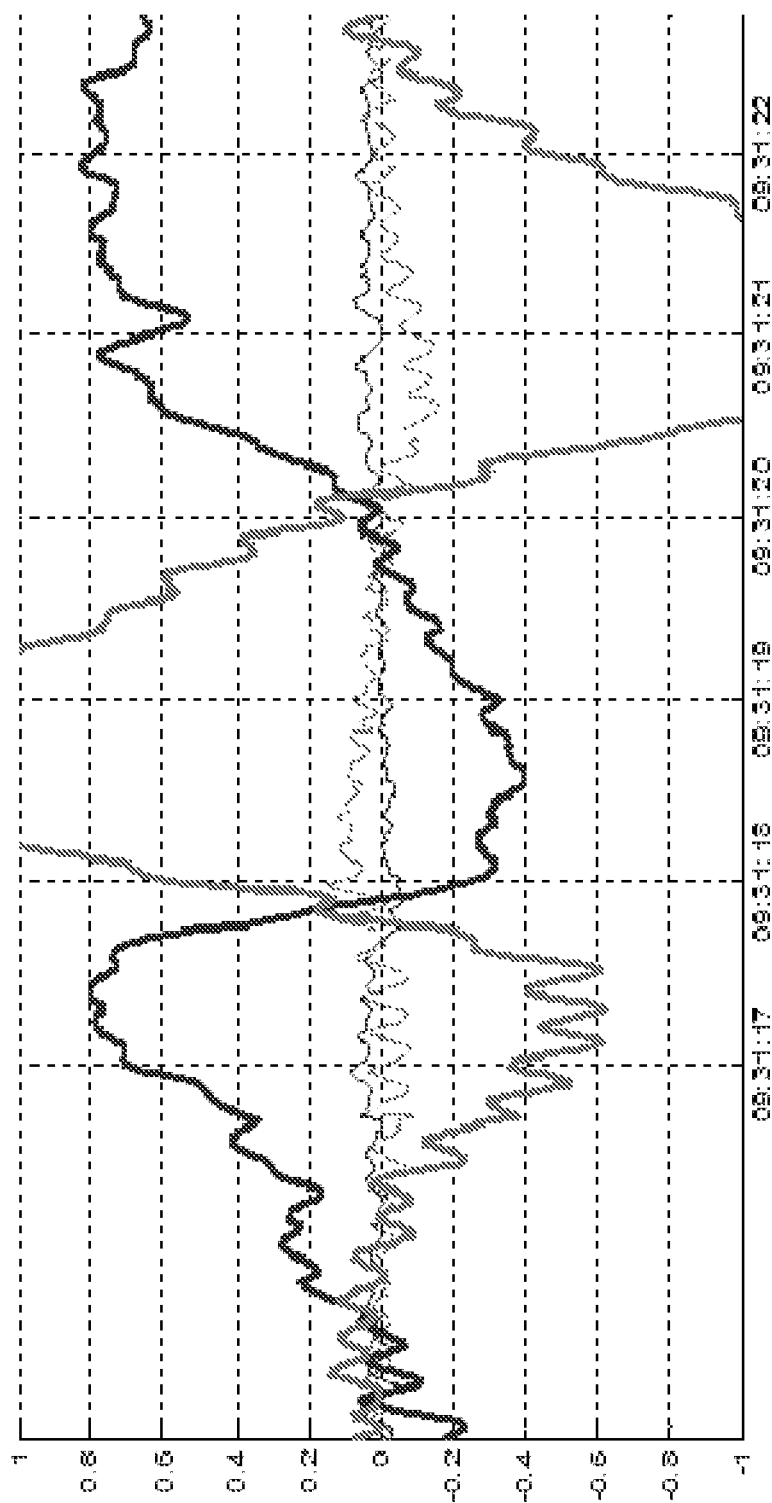

FIG. 4 illustrates velocity attribute determined by short time integration of the acceleration data, the dog's velocity can be determined in three-directions, although only they and z velocity components are shown here.

Figure 5:
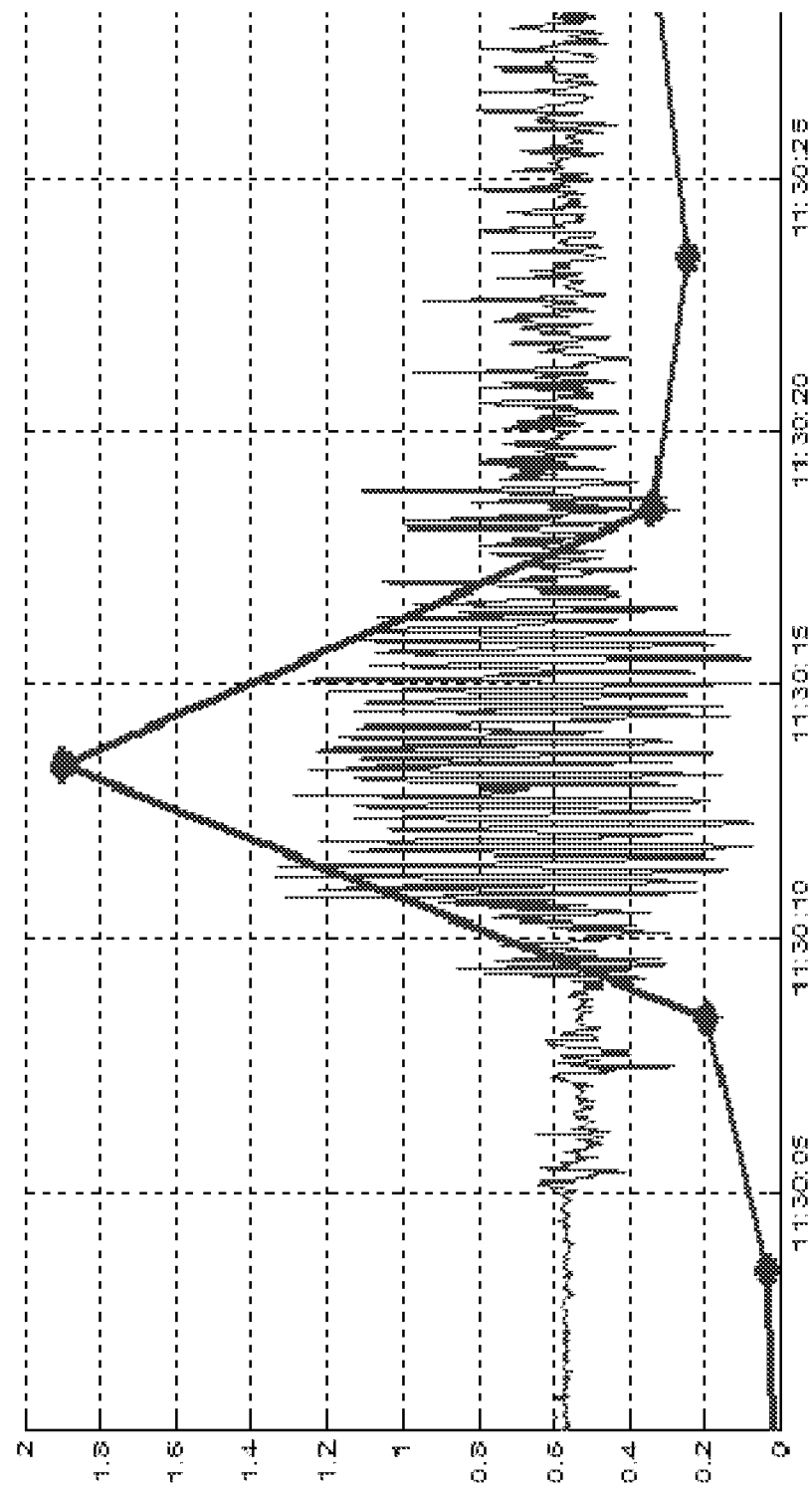

FIG. 5 shows relation of frequency attribute with respect to acceleration data. In this figure the frequency attribute of about 1.8 indicates walking for a corresponding breed and dog weight.

Figure 6:
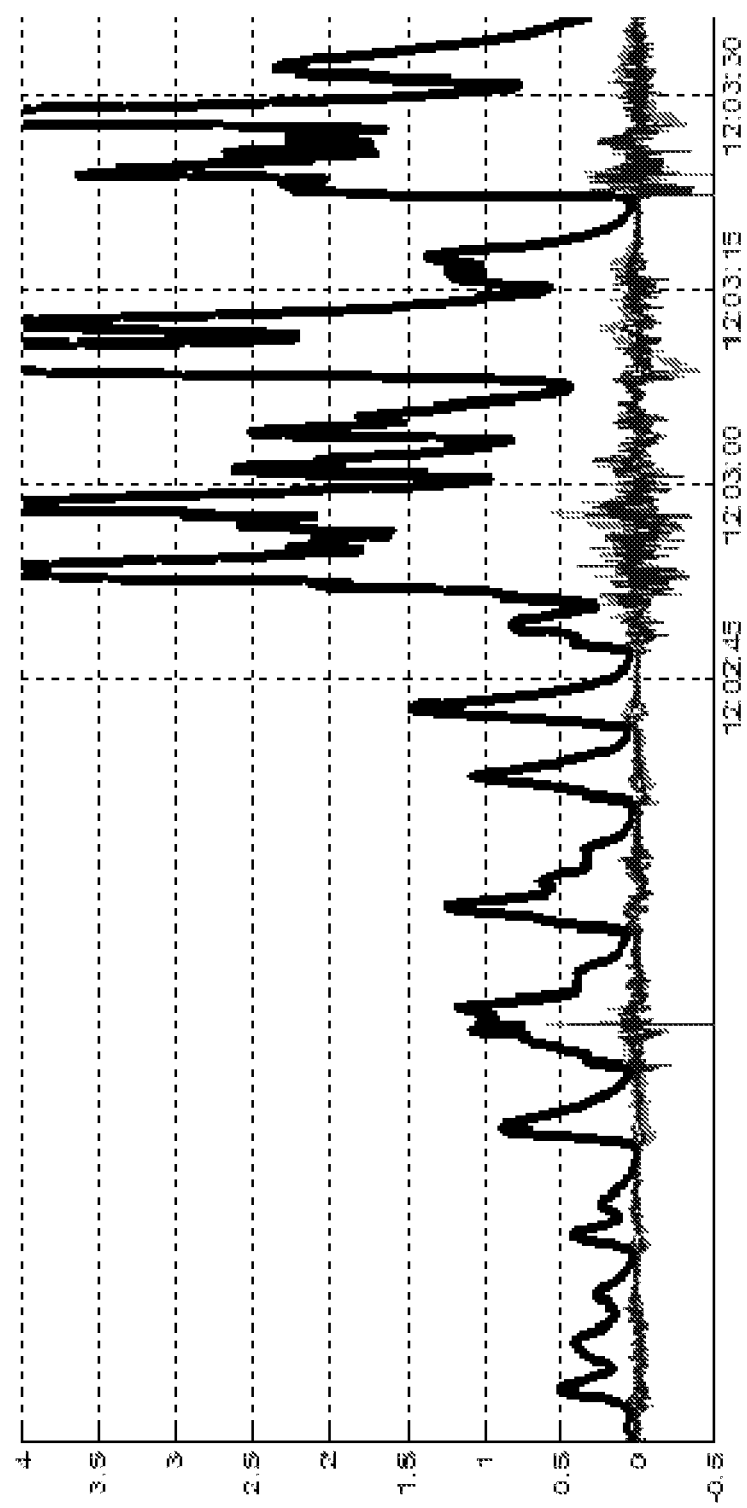

FIG. 6 shows variation of the energy attribute as determined by integration of power. As shows, the dog starts at relatively low energy and is idle. Higher level of energy, of about 1 in the corresponding units, indicates excitement, and higher levels, of about 4 indicate eating or other energetic activity.

It should be noted that the attributes illustrated in the figures and corresponding relations to the dog's behavioral states are brought here as examples and generally the analysis system may utilize a set of plurality of determined attributes to determine the dog's behavioral states. As indicated above, the behavioral analyzer may generally utilize appropriate machine learning techniques based on one or more training database.

Thus, the present invention provides a system, method and corresponding software for collecting data about pets' behavior and analyzing the collected data in view of additional household data to thereby provide indications about the pet's states. It should be noted that the technique of the present invention may utilize local element such as sensor unit and appropriate data receiver in combination with remote sever for data processing and/or local processing as the case may be.

The invention claimed is:
1. A system for condition analysis of a household pet, comprising:
 a primary sensor unit attached to said pet, said sensor unit comprising:

at least one 3D accelerator sensor attached to said pet; and a control unit connected with said 3D accelerator sensor and configured to collect acceleration data indicative of selected movements from said sensor, said control unit configured to perform an initial analysis of said collected sensor data;

at least one secondary sensor unit configured to sense location data pertaining to said pet's caretaker; and an analysis unit communicating with said control unit and with said at least one secondary sensor unit, said analysis unit configured to upload said collected sensor data and to receive additional data pertaining to said pet's caretaker location and to said pet's historical movement data, and to define said pet's condition accordingly by neutralizing effects of said additional data, wherein the data collection rate from the sensor is selected in accordance with at least said initial analysis results.

2. The system of claim 1, further comprising a first electronic communication device (ECD) configured to communicate with said analysis unit, said first electronic communication device (ECD) configured to receive and store historical movement data for a plurality of pets and to provide said data to said analysis unit.

3. The system of claim 1, further comprising a second electronic communication device (ECD) carried by said caretaker, said second electronic communication device (ECD) configured to communicate to said analysis unit at least part of said additional data.

4. The system of claim 3, further comprising a third electronic communication device (ECD) configured to run a user application for receiving and displaying said analysis results.

5. The system of claim 4, wherein said second and third electronic communication devices (ECD) comprise a single electronic communication device (ECD).

6. The system of claim 3, wherein said second electronic communication device (ECD) is configured to provide data selected from the group consisting of: global positioning of said caretaker and motion pattern of said caretaker.

7. The system of claim 3, wherein the uploading time of said sensor data is determined according to a learning curve of the proximity times of at least one of the analysis unit and the second electronic communication device (ECD) to said sensor unit.

8. The system of claim 1, wherein said analysis unit comprises an attribute extraction module configured to extract physical attributes of the pet's behavior.

9. The system of claim 8, wherein said physical attributes comprise head orientation and movement related attributes.

10. The system of claim 9, wherein said movement related attributes comprise at least one of: velocity, energy and power.

11. The system of claim 8, wherein said physical attributes comprise at least one of frequency related attributes and temporal attributes.

12. A method of behavioral analysis of a household pet comprising:

providing a primary sensor unit attached to said pet;

collecting from said primary sensor unit acceleration data indicative of selected movements of said pet;

performing an initial analysis of said collected movement data;

providing at least one secondary sensor unit;

receiving from said at least one secondary sensor unit additional data pertaining at least to the location of said pet's caretaker;

receiving data pertaining to said pet's historical movement; and defining said pet's condition accordingly by neutralizing effects of said additional data, wherein the data collection rate from the sensor is selected in accordance with at least said initial analysis results.

13. The method of claim 12, wherein said initial analysis comprises determining a moving average of the first derivative of the collected acceleration data and determining if the moving average is greater than a predetermined threshold.

14. The method of claim 13, wherein determining the moving average comprises utilizing varying weights.

15. The method of claim 12, wherein said acceleration data includes high frequency varying data and low frequency varying data.

16. The method of claim 15, wherein said high frequency varying data is indicative of the pet's movement, and wherein said low frequency varying data is indicative of orientation of the sensor unit.

17. The method of claim 12, wherein said defining said pet's condition comprises utilizing machine learning.

* * * * *